(12) United States Patent
Rosenbaum et al.

(10) Patent No.: US 10,918,596 B2
(45) Date of Patent: Feb. 16, 2021

(54) ORAL DELIVERY SYSTEM AND METHOD

(71) Applicant: MEDICAL FOODS RX, LLC, Las Vegas, NV (US)

(72) Inventors: Todd Rosenbaum, Scottsdale, AZ (US); Jim Klemaszewski, Mesa, AZ (US)

(*) Notice: Subject to any disclaimer, the term of this patent is extended or adjusted under 35 U.S.C. 154(b) by 88 days.

(21) Appl. No.: 16/182,445

(22) Filed: Nov. 6, 2018

(65) Prior Publication Data

US 2019/0307675 A1 Oct. 10, 2019

Related U.S. Application Data

(60) Provisional application No. 62/652,871, filed on Apr. 4, 2018.

(51) Int. Cl.
| | |
|---|---|
| A61K 9/00 | (2006.01) |
| A61K 36/28 | (2006.01) |
| G01N 21/25 | (2006.01) |
| A61K 31/05 | (2006.01) |
| G01N 33/15 | (2006.01) |
| A61K 31/352 | (2006.01) |
| B65D 65/46 | (2006.01) |
| A01N 65/00 | (2009.01) |

(52) U.S. Cl.
CPC .............. *A61K 9/006* (2013.01); *A01N 65/00* (2013.01); *A61K 31/05* (2013.01); *A61K 31/352* (2013.01); *A61K 36/28* (2013.01); *B65D 65/46* (2013.01); *G01N 21/255* (2013.01); *G01N 33/15* (2013.01)

(58) Field of Classification Search
CPC ...... B65D 65/463; A01N 65/00; A61K 9/006; A61C 15/00
See application file for complete search history.

(56) References Cited

U.S. PATENT DOCUMENTS

| | | | |
|---|---|---|---|
| D688,005 S | 8/2013 | Marold | |
| 8,753,696 B1* | 6/2014 | Lewis | A61K 36/185 424/725 |
| 9,060,833 B2* | 6/2015 | Marold | A61C 15/02 |
| 2006/0201531 A1* | 9/2006 | Brown | A61K 8/731 132/321 |
| 2016/0207679 A1* | 7/2016 | Jackson | B65D 65/463 |

* cited by examiner

*Primary Examiner* — Dah-Wei D. Yuan
*Assistant Examiner* — Andrew J Bowman
(74) *Attorney, Agent, or Firm* — Chris Tanner; TannerPatent.com

(57) ABSTRACT

A system and method for infusion of active ingredients into a delivery device is disclosed. The active ingredients can be loaded into a variety of oral delivery devices, including but not limited to toothpicks, tongue depressors, ice cream sticks and cocktail stirrers. In an embodiment, these delivery devices might be made from various types of wood, one non-limiting example being birchwood. These oral delivery devices can be used to deliver various of the following active ingredients along with inactive ingredients such as flavor, natural, and/or artificial sweeteners, as well as other items not explicitly shown in this list: nicotine, smoking cessation products, caffeine, tetra hydro cannabinol (hereinafter referred to as THC), cannabidiol (hereinafter referred to as CBD), and dietary supplements.

11 Claims, 13 Drawing Sheets

FIG. 2 (cross-section of delivery device 104)

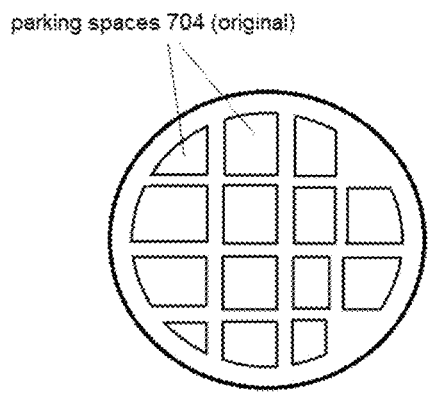
FIG. 7A (base unaltered delivery device 104 cut at a 90-degree cross-section)
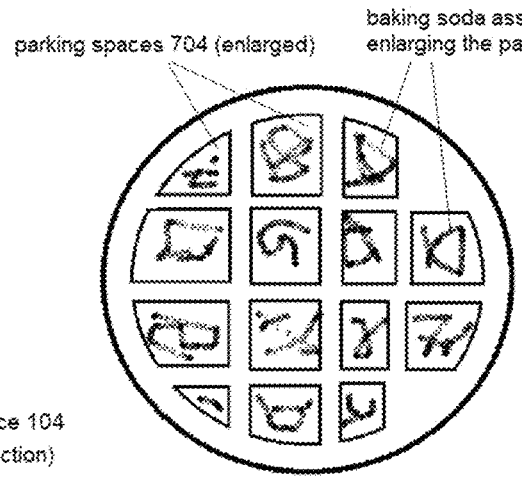
FIG. 7B (after pre-treatment, but un-rinsed)
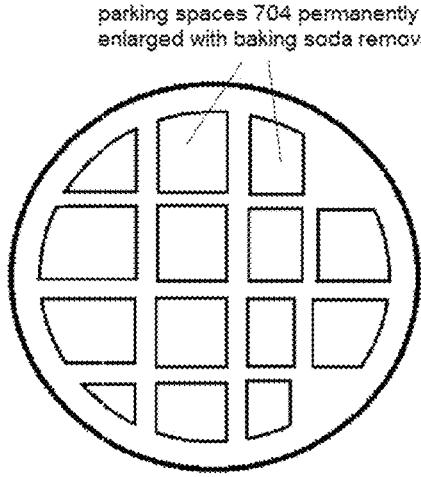
FIG. 7C (post-rinsing)

ORAL DELIVERY SYSTEM AND METHOD

BACKGROUND

As discussed herein, a toothpick is a small stick of wood used to remove food or other foreign substances from the teeth. It serves as an example of a cellulose-based substrate that can be infused with pharmaceuticals, as well as other key ingredients.

There exist several methods of delivering pharmaceuticals to patients, including but not limited to injection via a needle (subcutaneously or intravenously, implantation, inhalation), eyedrops, or orally. Oral delivery of pharmaceuticals includes drinking a fluid, for example acetaminophen in liquid form, a pill, tablet or capsule, a lozenge or gum. While each of these methods has a distinct application, none of them allow for micro-dosing, or dosing to be paused and restarted, multiple times if necessary. Furthermore, several of these delivery systems are difficult for people with dysphagia, and may result in choking or aspiration, for example with children, the elderly or those with swallowing disorders.

Accordingly, there remains a need to produce a delivery system with a greater ability to hold and to effectively deliver pharmaceuticals in small dosages in a way that can be delivered iteratively.

SUMMARY OF THE EMBODIMENTS

The delivery device described herein can be a toothpick or other device, and can be pretreated to increase porosity, decrease hardness, and/or prepare the substrate to hold the desired pharmaceutical, for example, by altering its pH, or to apply non-pharmaceutical ingredients (e.g., flavoring, binding agents, masking agents, etc). The pretreatment may be performed by administering a solution to the substrate, and also involves increasing and/or decreasing the pressure, temperature and/or humidity of the environment surrounding the delivery device to achieve desired penetration by the pretreatment solution into the delivery device.

In an embodiment, the pretreatment of the solution is an acidic and/or basic solution, depending on the desired outcome characteristics (e.g., porosity, pH, density, polar, non-polar, hydrophilic or hydrophobic, etc.) of the substrate prior to treatment. Further, a solvent(s) of the treatment solution is/are polar and/or non-polar, depending on the nature of the desired ingredients. The pre-, treatment, and post-treatment solutions can be either agitated, flowing or stationary during manufacture and application.

Within the embodiments herein, at least the following components may be included: solvent, flavoring, masking agents, preservatives, binding agents, sweeteners, and/or weighting agents. During manufacture and finishing\infusing the substrate, there may be several orders of applications of these elements.

For example, in an embodiment, it is possible to apply the binding agents to the substrate only after applying the sweeteners. Further, it is possible to make an embodiment of the pre-treatment prep-solution of containing only masking agents and preservatives. Meanwhile, at the same time, it is possible to make up another prep-solution of e.g. weighting agents, and applying one prep-solution before/after/simultaneous with the other.

This disclosure is directed to the infusion of active ingredients in dosage by volumes as a percentage of wood weight and precisely load such volumes in a variety of oral delivery devices, including but not limited to toothpicks, tongue depressors, ice cream sticks and cocktail stirrers. In an embodiment, these delivery devices might be made from various types of wood, one non-limiting example being birchwood.

These oral delivery devices can be used to deliver various of the following active ingredients along with inactive ingredients such as flavor, natural, and/or artificial sweeteners, as well as other items not explicitly shown in this list: nicotine, smoking cessation products, caffeine, tetra hydro cannabinol (hereinafter referred to as THC), cannabidiol (hereinafter referred to as CBD), dietary supplements, mechanisms for reducing drymouth (xerostomia), and/or compound pharmaceuticals.

A person's throat narrows with age. Even with sufficient water present during ingestion, pills can still get stuck in the throat. The embodiments herein contemplate a way to deliver medications without requirement of swallowing an entire pill and binder. Examples of xerostomia, also known as dry mouth or cotton mouth, is an abnormal dryness of the mouth resulting from the decreased secretion of saliva. Dry mouth causes include but are not limited to smoking & alcohol use, prescription medications, auto-immune diseases, chemotherapy and radiation, dehydration, and tooth decay. soldiers in e.g. desert regions, or the elderly. Also, many medications (e.g. anti-histamines) cause dry mouth. To address this, Jambu oleoresin can be included along with natural sweeteners sucralose and xylitol (among other ingredients) to stimulate generation of saliva.

BRIEF DESCRIPTION OF THE DRAWINGS

FIGS. 7A, 7B, and 7C show a summary of a transition of a delivery device during a pre-treatment process.

DETAILED DESCRIPTION OF THE PREFERRED EMBODIMENTS

The embodiments herein are can be made from a variety of wood products. However, the example of birchwood will be a primary example, although the embodiments herein should not be considered as limited thereto.

Figure 1:
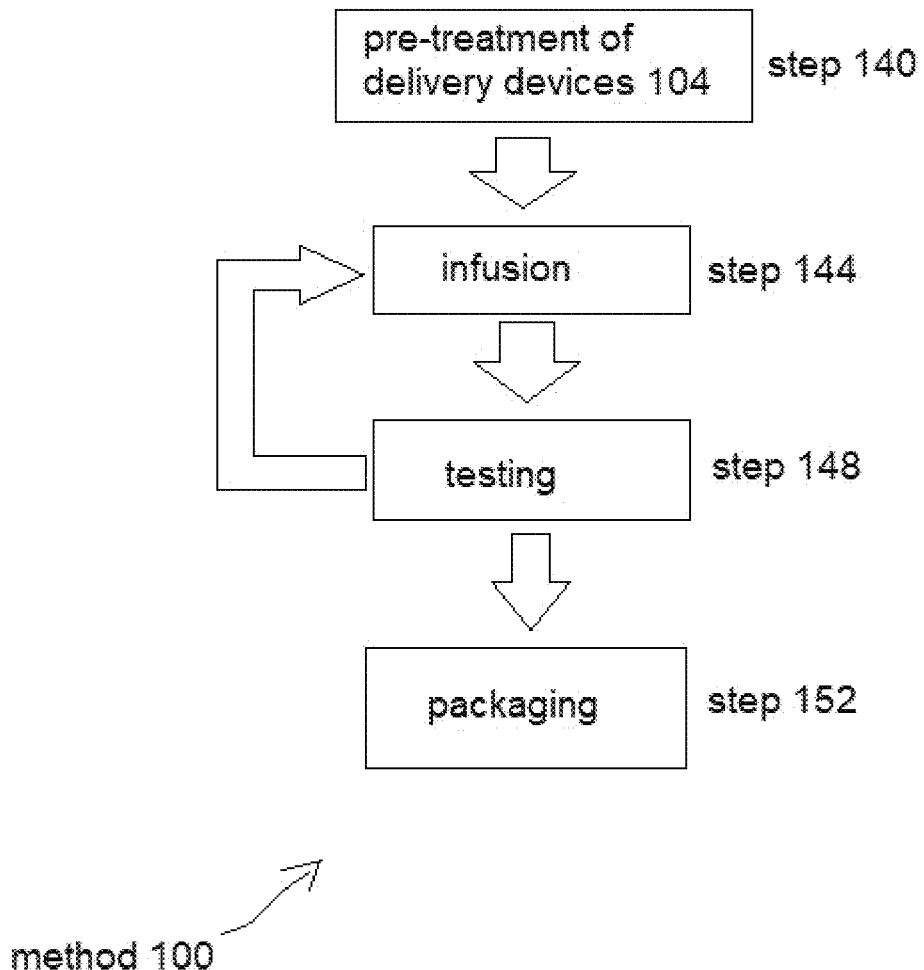
FIG. 1 shows an example overall method 100 of infusing ingredients into a delivery device.

FIG. 1 shows an example overall method 100 of infusing ingredients into a delivery device 104 (e.g. toothpick). Step 140 involves the pretreatment of a plurality of delivery devices 104. At step 144, the delivery device 104 is infused with its ingredients. At step 148, the delivery device 104 is tested to ensure the ingredients have been infused to the proper/target proportions or quantities. Depending on the testing, the delivery device 104 is either re-infused, or then engages a packaging step 152.

Figure 2:
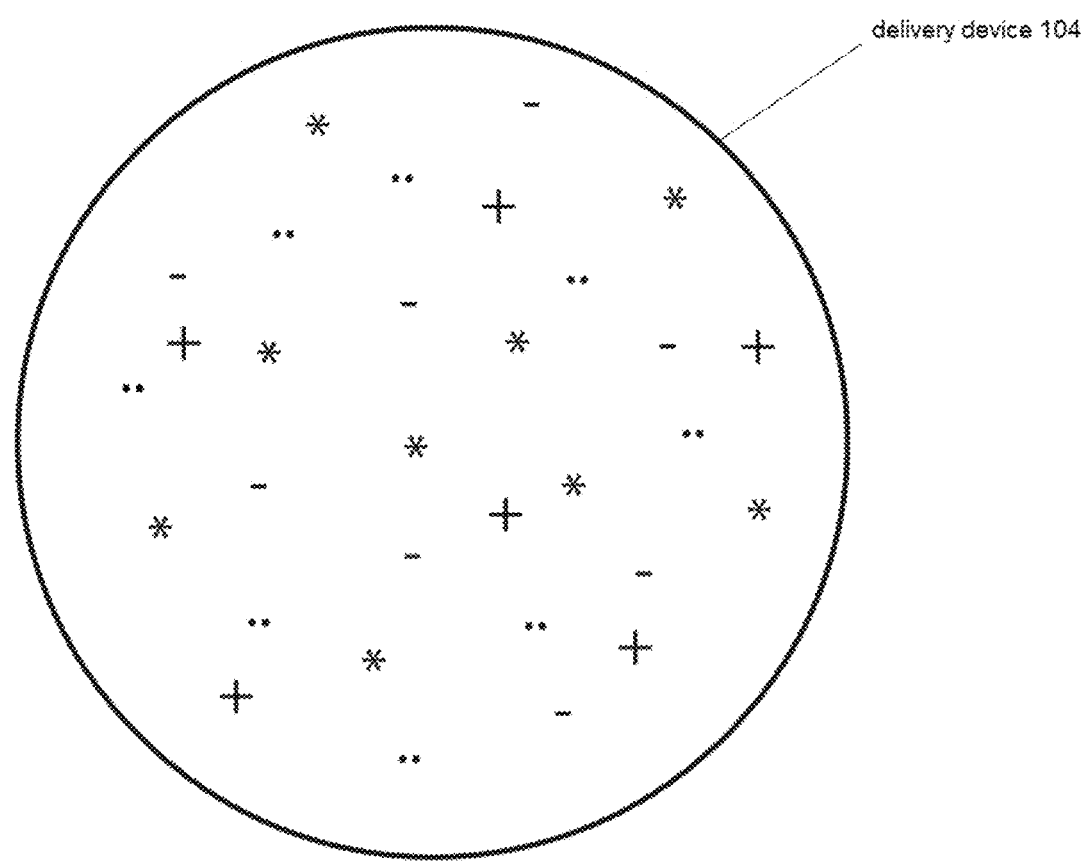
FIG. 2 show a cross-section of a delivery device.

FIG. 2 show a cross-section of a delivery device 104. The purpose of FIG. 2 is to depict an example post-infusion distribution of the ingredients throughout a delivery device 104. From FIG. 2 it is apparent that the ingredients are evenly distributed through the entirety of the delivery device 104.

Figure 3:
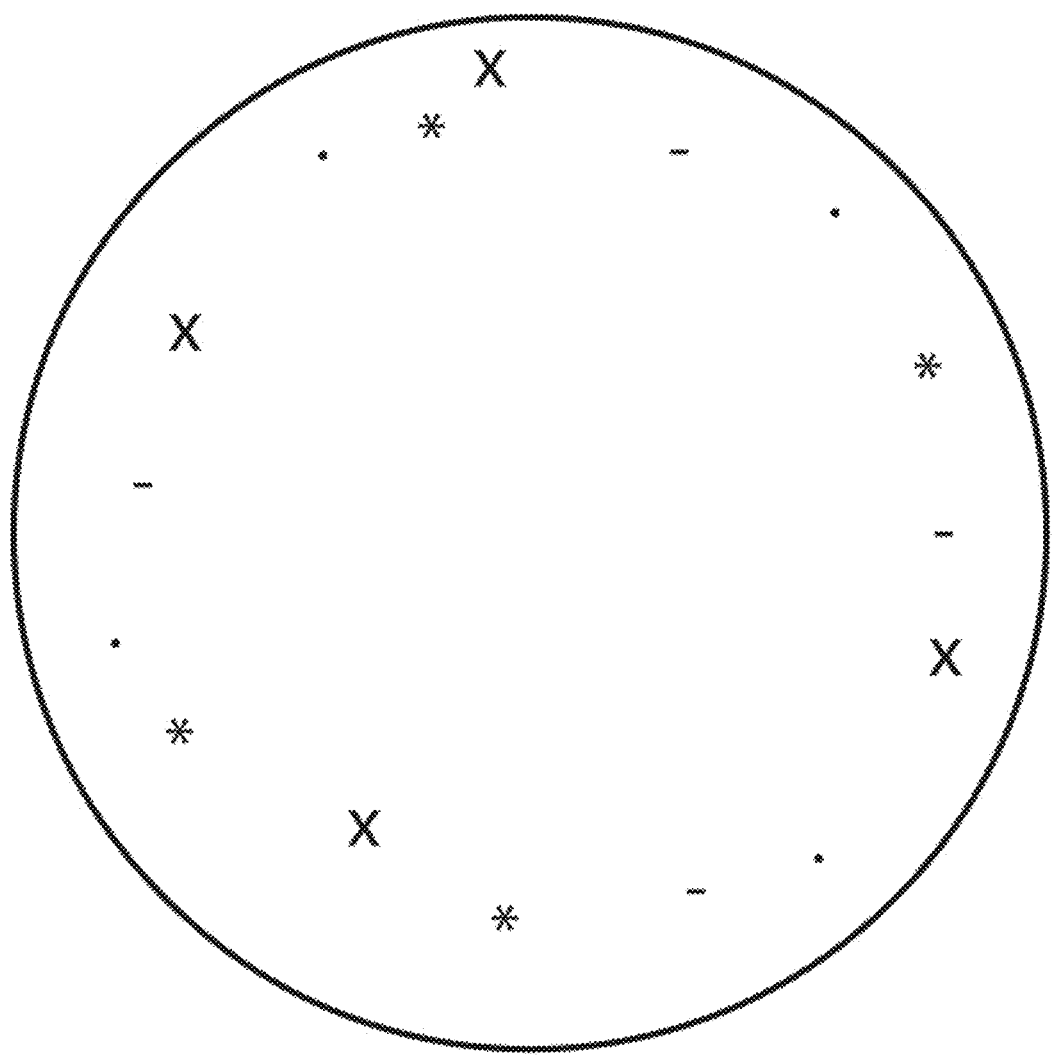
FIG. 3 shows a Prior Art embodiment.

FIG. 3 shows a Prior Art embodiment, showing surficial application of ingredients (e.g. flavorings or oils) on the surface-only areas of a toothpick, and the relatively ineffective or weak surface-only or near-surface-only distribution thereof.

Figure 4:
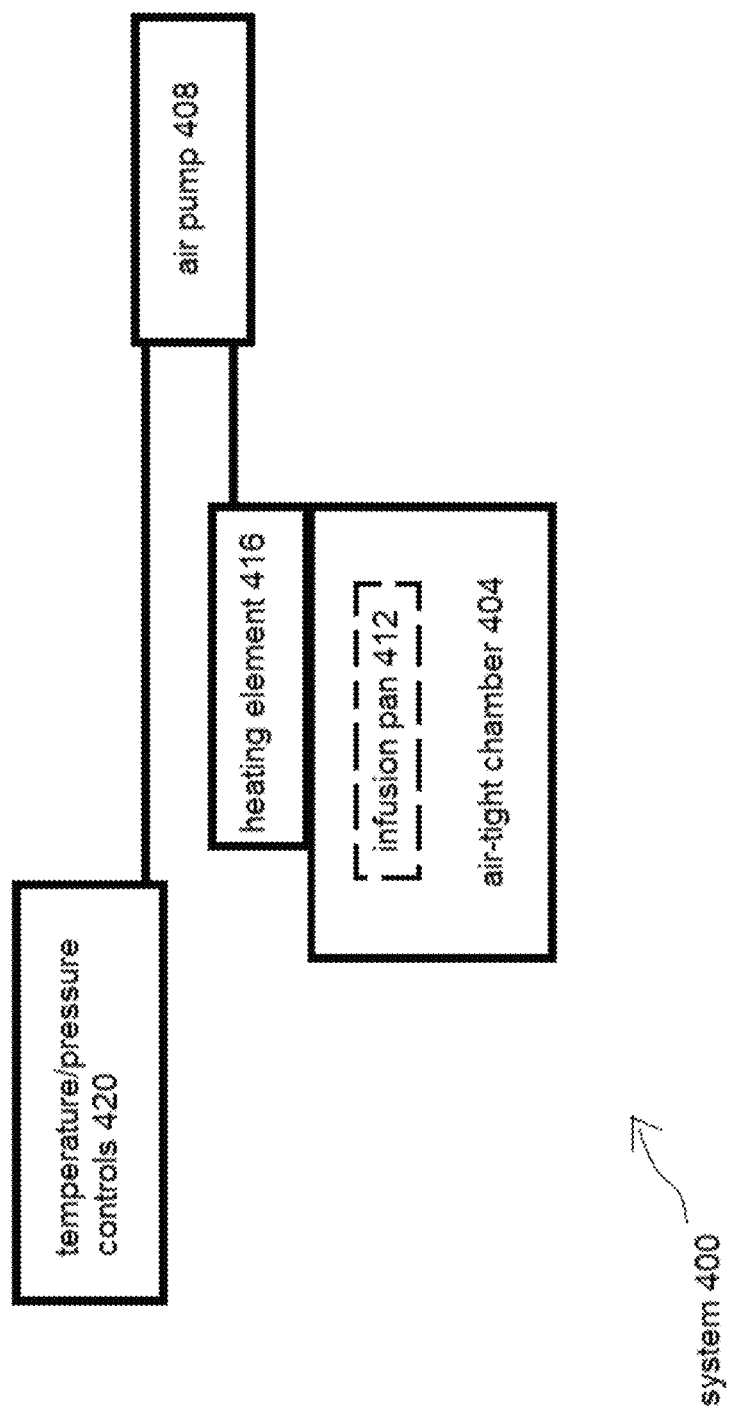
FIG. 4 shows an example pressure- and temperature-controlled environment used in producing the embodiments described herein.

FIG. 4 shows an example pressure- and temperature-controlled environment used in producing the embodiments described herein. Specifically, FIG. 4 shows a system 400 for producing various embodiments of a delivery device 104. The system 400 comprises an air-tight chamber 404, one or more infusion pans 412, an air pump 408, a heating element 416, and temperature/pressure controls 420. The infusion pan 412 is drawn in dashed lines because it is sometimes located inside the air-tight chamber 404, but at different stages of the manufacturing process, will be located outside the air-tight chamber 404.

Figure 5:
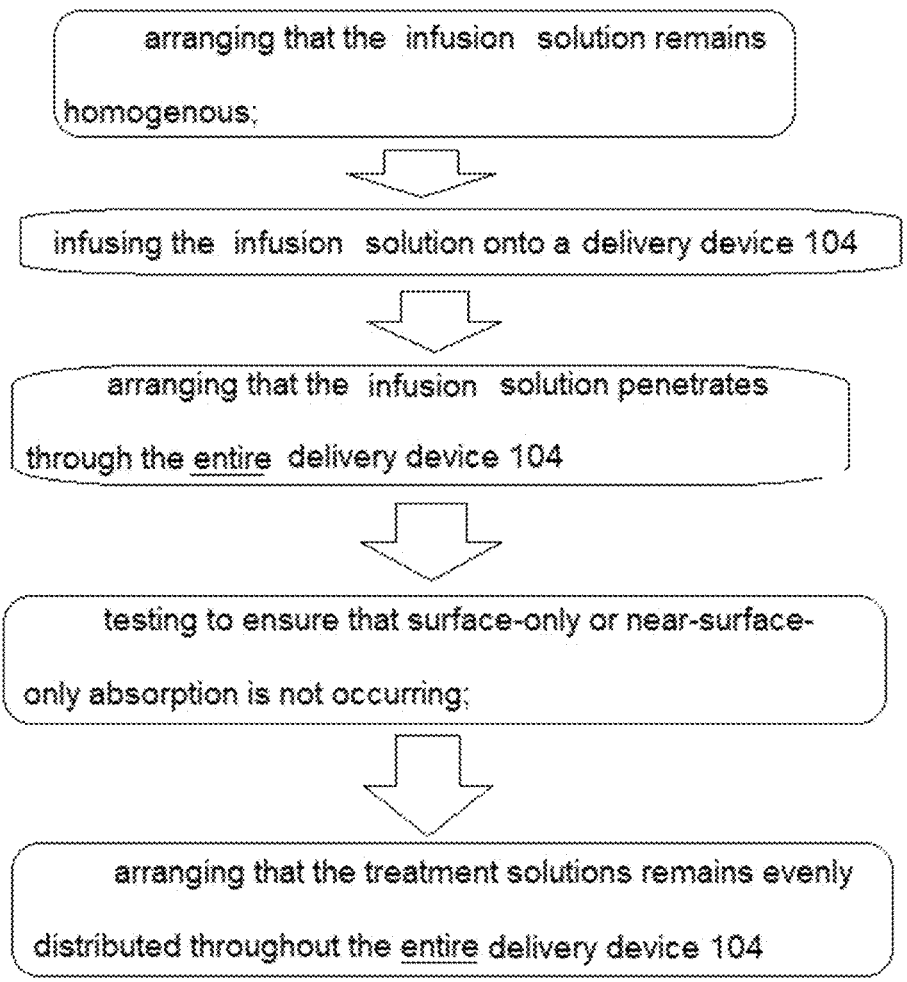
FIG. 5 shows an example method of manufacture.

FIG. 5 shows an example method of manufacture.

How Jambu Affects the Oral Cavity

Various of the embodiments described herein use Jambu oleoresin, a concentrated extract of Spilanthes *acmella* (hereinafter referred to as "Jambu", capitalized because it is a term of art). This botanical is known as "the toothache plant" and has been used to alleviate mouth pain for centuries. Additionally, spilanthol has strong saliva-inducing effects and can act as a mild anesthetic. Jambu can cause a tingling sensation in the mouth and lips often experienced during salivation.

It is well-known that the oral cavity (under the tongue) generates saliva at a high rate. The Jambu component of the embodiments herein is significant because of its activity outside the oral cavity. However, the cheeks, upper tongue surface, and lips are important for adding as much as 60% more saliva but doing so sublingually (i.e. not using the oral cavity). Due to Jambu providing excitation to the mucosal lining, more saliva is excreted through nerve paths within the cheeks, tongue, and lips. These nerve paths remain open for the Jambu to keep creating that tingle, but keeping the nerve paths open helps facilitate an active ingredient (e.g. THC, CBD, other) to enter the mucosal lining and be absorbed into the bloodstream. This feature is important for several of the embodiments herein, including for example the dry-mouth embodiment.

The end result is that the various Jambu-related embodiments disclosed herein (not all embodiments herein use Jambu) are potentially 60% faster than just sucking a sweetener, e.g. xylitol or sucralose. The 60% increase occurs from using these three more mucosal lining surfaces that normally do not get used by conventional flavored toothpicks.

If one doesn't apply Jambu properly, the result can be an overstimulation of the entire face, but without the excretion of more saliva. The goal is to get that Jambu inlaid between the various flavors and active ingredients. Achieving this required considerable testing, experimentation, and measurement.

The Jambu already being used for dry mouth creates a tingle. This gives rise to the expression "feel the tingle", because that's the sensation experienced by a user of the embodiments described herein. Translating to medical terms, the tingle indicates how Jambu fires off the nerve paths on the inside of the mouth.

The embodiments herein combine the sweeteners that are coming into a mouth using a sucking fashion with the Jambu tingle, as Jambu stimulates salivation. The result is an efficient delivery platform, which is imperative from a consumer-mindset and mouthfeel standpoint. The delivery device 104 thus medicates through a sublingual platform.

Relationship of Wood, Baking Soda, and "Parking Spaces"

The embodiments herein make extensive use of baking soda, also known as sodium bicarbonate, symbolized by $NaHCO_3$. The embodiments of the delivery device 104 described herein are pre-treated in distilled water with an aqueous baking soda solution. The wood absorbs the baking soda, expands, and re-shapes itself to create "parking spaces" for other ingredients to be inserted later, in a process known as infusion. The baking soda also prevents the wood from molding during the drying state. These parking spaces house the later ingredients in such a way that (during manufacturing) absorption and retention of the ingredients described herein is increased. Further, during use, when saliva is applied to these parking spaces, a user-controllable and user-detectable release of the ingredients is facilitated.

The delivery device 104 is then placed in a vacuum, which serves to increase the absorption capacity (improved "parking spaces") of the wood. The delivery devices 104 are then rinsed to decrease the concentration of baking soda, so as not to interfere with the other ingredients. Thus, the baking soda is removed, but the parking spaces remain.

In certain embodiments, a minor amount of baking soda may be intentionally left within the delivery device 104, which would have the effect of slightly lowering the pH of the delivery device 104 when saliva is applied. This alteration to pH can be beneficial for taste and user-experience considerations. In embodiments where pH is not desired to be lowered, extra rinsing can occur to remove any baking soda not removed by the original heated or climate controlled drying environment. The embodiments herein also contemplates ways to raise the pH.

In an embodiment, a preferred concentration of baking soda solution may be 1 to 5 moles per unit of water. Increasing this preferred concentration may have the effect of excessive softening of substrate (e.g., toothpick). Meanwhile, decreasing this preferred concentration may have the effect of limiting the amount of active ingredient that can be absorbed.

Most wood contains lignins in one form or another, which is important in the formation of cell walls, especially in wood and bark. This is because lignins lend rigidity and do not easily rot. The "parking space" metaphor used frequently herein partly relates to lignin properties of the wood within the delivery device 104.

Using a metric that's easy to understand, assume that at most, 3 rain-drops of all fluids used can fit within the toothpick (space constraint). Knowing that only 3 rain drops of space are available, 80-90% of that space should be for e.g. the active ingredient, leaving at most 10-20% available for flavorings e.g. coffee, chocolate, lemon-lime, or other. Assume a dosage of 30 mg of caffeine, but also assume putting it into 0.15 milliliters (3 rain-drops of liquid). The result is a much better concentration of ingredients, more manageable from a manufacturing and stability standpoint, more controllable and testable, and more consistently repeatable.

A usable medical product also works as a dental product, and has a familiar point on it. The birchwood arrives to market within 14 to 16 weeks of harvesting.

The birchwood plant by itself is porous by nature and already contains a considerable amount of water. It is necessary to replace water with oil-based ingredients, since they don't naturally go together. The answer is, create parking spaces and replace ingredients. As such, the toothpick's evolution of being in birchwood was significant because its friendly for the mouth.

The embodiments herein sometimes go by the slogan "just suck it", because sucking at the delivery device 104 like a lollipop makes each layer of the wood become accessible, which in turn allows the user to intake all layers of the submerged ingredients, with the assistance of the user's teeth. In other words, "just suck it" will get the user to new parking spaces that conventional products do not have. At that point, $2^{nd}$-layer territory, the outermost layer may have already been broken down, both by saliva, teeth, and suction pressure. The mild imprint of teeth will lead to getting to the parking spaces within the more interior second layer, and a much longer and more satisfying user experience.

There exists a connection between the wood and the Jambu. The Jambu is a natural extract that comes from a plant, and thus behaves very friendly with the wood.

The methods herein change the porosity and change the density of the delivery device 104, whether made from birchwood or other wood-base. The delivery device 104 is porous by nature, and already holds 23-25% water before the treatment.

The delivery device 104 is wood, so first flood it with water to fatten it up, as wood absorbs water. However, when wood absorbs water it is susceptible to molding, usually when it dries. If not cured properly, once fattened, before drying, mold can grow in these parking spaces. To address this, occupy the parking spaces with something else. Use baking soda as a "spacer" in a first process.

Once the new delivery devices 104 are submerged, fully submerged (that is, the infusion liquid being more than 130% the maximum height of the delivery devices 104), then put through an infusion process. Change the pressure on the combination, forcing the water into it with the baking soda, thus forcing parking spaces into e.g. the natural birchwood. At the time the vacuum releases, the baking soda has taken the place of the water. Then, the baking soda creates parking spaces so when the delivery device comes out and is rinsed and drained and dries as it dries and hardens again, mold cannot form therein. Thus, baking soda prevents the delivery device 104 from molding as the parking spaces are created.

Another challenge is that using e.g. 30K raw delivery devices 104 will absorb a specific amount of fluid, e.g. 2 L of fluid. It is necessary to ensure total immersion occurs. To address this, the embodiments herein also include a customized pan such that it is possible to take a toothpick from/in rectangular boxes so that the raw wood is lined up uniformly.

Lift out the raw delivery devices 104 in a band, e.g. 30,000 at a time, fit them into the specially-designed pan, put in solution, infuse in oven, pull out, either in the pan or out, tighten the band, pull them out, put that into a drying well, force air at them. In an embodiment, it is possible to locate three different pans in one oven. As stated, the embodiments herein include the specially-formulated customized pan sized to accommodate specific sizes and heights of delivery devices 104.

The channels of the wood are not now occupied by a by solid state matter, not just water anymore. Then, in an embodiment let the delivery devices 104 dry over 24 to 36 hours, where they can become hardened enough and the baking soda has dried inside of it. Then, rinse out the remaining baking soda from both the exterior and the interior of the delivery device 104.

Figure 6:
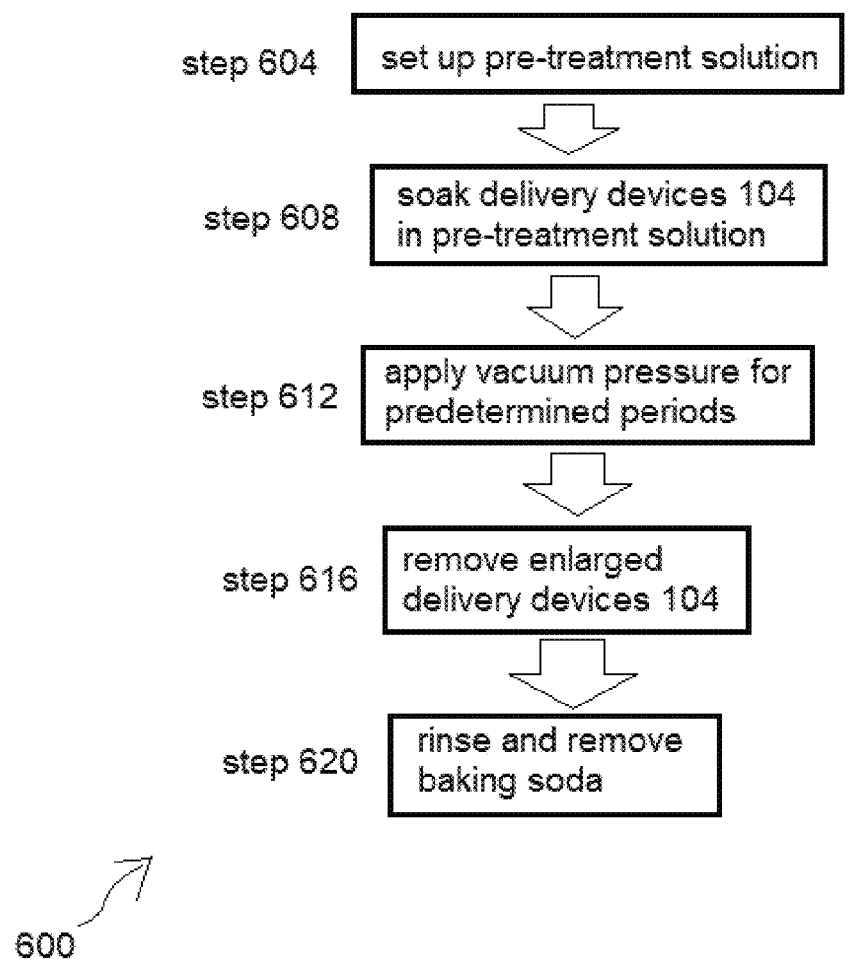
FIG. 6 shows an example method of pre-treatment.

The above is diagrammed and summarized in FIG. 6, by the example method 600 shown therein. At step 604, a pre-treatment solution is set up, containing at least baking soda in various predetermined amounts. At step 608, a plurality of delivery devices 104 are soaked in the pre-treatment solution. At step 612, vacuum pressure and potentially heat is applied for predetermined periods. During this time, the plurality of delivery devices 104 are enlarged in size. At step 616, the enlarged delivery devices 104 are removed, and at step 620, the enlarged delivery devices 104 are rinsed, partly to remove the baking soda from the exterior and interior of the delivery devices 104.

FIGS. 7A-7C show a rough, approximate summary of this transition. FIG. 7A shows what parking spaces 704 that may exist in the original wood and lignin interior of a typical delivery device 104. FIG. 7B shows the changes that occur within the delivery device 104 after the pre-treatment process described herein. Note that the parking spaces 704 are enlarged, indeed the entire delivery device 104 is enlarged. At this time within FIG. 7B, baking soda remains in at least some of the parking spaces 704. FIG. 7C shows the intact, post-rinse delivery device 104, with the parking spaces properly enlarged, and the baking soda removed.

Infusion

The ingredients discussed herein have different weights and different variations. Because of this, various steps are taken to prevent their separation during an infusion process. In an embodiment, one practice is to submerge the delivery devices 104, dry them, submerge those dried delivery devices 104 again, and put them back into the vacuum oven. In some embodiments, the delivery devices 104 are run through the vacuum oven yet, thus further forcing the new ingredients into the delivery devices 104 (where applicable). In an embodiment, ethanol is used to act as one potential solvent for effective delivery of the ingredients.

In one example embodiment, it is possible to release the pressure within the vacuum oven (air-tight chamber 404) and make one more transfer at conventional (ambient) pressure. At conventional (ambient) pressure, the ethanol volatilizes (vapes off), so there's no traces of any of any ethanol remaining in the delivery device 104. The intent is that the active ingredients will locate themselves in the parking spaces in the delivery device 104. Then, it is possible to drain the delivery devices 104 and let them dry for 24 to 36 hours. At that point, the end result is a tasty delivery device 104 (non-medicated version).

Various of the embodiments herein infuse ingredients into the delivery device 104 once, while other of the embodiments may infuse twice. The reason for a multi-infusion is to achieve certain predetermined goals regarding precision of amounts loaded into the delivery device 104. Infusion can result in diffusion. A second infusion should still achieve the same level of penetration as the first infusion. With a second infusion, a diffusion process will carry ingredients all the way through. A second infusion can "flow past the parking spaces" that are filled, and yet still have sufficient kinetic energy to continue flowing to empty parking spaces.

The medicated embodiments herein are similar, other than the fact of using oils, e.g. flavor terpenes like lemons, oranges, and citrus, or active ingredients like the medical marijuana products e.g. THC oil or CBD oil. These are much heavier than a terpene oil that exists inside flavoring.

If the medication is ibuprofen or Viagra® or anything else that is a compound pharmaceutical, then consistency is assured. However, with medical marijuana, consistency is not assured. As will be discussed in more detail herein, factory extraction of e.g. THC oil is a mere hobby for many of the vendors, the people that are doing this for fun versus as in a professional trade. Those people are hobbyists at best, merely entertained by their quasi-business (actually only an expensive hobby). The medical side of the embodiments herein are different because carrying a specific verifiable volume is needed. The embodiments herein strive to make the user experience and performance consistent.

Post-infusion, a delivery device 104 is fattened up some, but still has stability as the wood fibers and lignin are still intact. Consequently, a post-infusion delivery device 104 can still be used as a conventional toothpick. The sharpened pencil shape at end is somewhat blunted from a typical toothpick shape. Still, the more water added, the more the toothpick is going to expand. After drying, the delivery device 104 will shrink back down, but the smallest it will ever get will be back to its post-infusion state, still approximately 22-25% fatter than its shape before pre-treatment.

In viewing a freshly harvested piece of untreated un-infused wood used in forming the delivery device 104, it is possible to see how tight the wood composition is, almost like a polished dining room table. However, the wood still is capable of a small bend. As such, the delivery device 104 will feel very firm in a user's mouth.

Next, after a first infusion process into the delivery device 104, the wood visually becomes more grainy. The processing described herein allows the pores (parking spaces) in the grains to be filled. Because of the tightness of the wood-grain (even after one or more infusions), the wood is unlikely to splinter, and unlikely to fragment.

Usage of the Delivery Device 104

The four most important traits of the embodiments described herein are discretion, portability, micro dosing, and sustainability. Micro dosing refers to how a user can orally ingest (active ingredients) in stages, stop, start, and begin again. The delivery device 104 described herein can be used anywhere anytime, at work, family settings, smoking restricted areas and any travel scenario. The last thing people are thinking is that a toothpick has any functional use such as medication in it of any kind.

In a THC or CBD smoking method, or vape technology, no less than 50% waste is released into the air, 25% of the inhaled product is released from the lungs. This leaves the end-user to receive only 25% of the active ingredient. Moving to edibles, an edible delivery system in most cases 30-35% is wasted from metabolism, again limiting the percent of the active ingredient reaching a user. In sharp contrast, the embodiments herein provide a suckable mechanism, beverage infusing embodiment, or tongue depressor embodiment for use as a delivery device.

Any plant, depending on how it was grown, will have different results and taste. If harvested improperly, or grown with solvents which is good part of the market for enthusiasts, there can be a resulting bitterness. The embodiments herein mask all of that. The embodiments herein have no taste or odor of THC. Avoid any taste or residue of marijuana whatsoever. No matter what packaging is used, with the embodiments herein one can open one a tube or any other form of packaging and never experience the smell of an active ingredient such as THC or CBD.

In the beginning, a decision was made to have a base formulation for numerous embodiments, but which always contained a varied percentage of the formulation for resolving dry mouth and acting as the delivery mechanism for such active ingredients. This base formulation includes Jambu which creates a tingle in the mouth. The Jambu activates the nerve paths of the mucosa lining in the cheeks, tongue and lips allowing additional saliva to excrete and at the same time allowing these lining to absorb such active ingredients. The tingle is temporary but can continue for example after taking the toothpick out. The tingle acting as a mild anesthetic will dissipate and fade away, but the saliva will continue for an average of 15-20 minutes. This is an important distinction over being a mere flavored toothpick.

The toothpick embodiments described herein can load up to 55 milligrams of active ingredients in one single delivery device. This includes THC, CBD, smoking-cessation, caffeine, nicotine, but also compound pharmaceuticals e.g. anything from ibuprofen to acetaminophens, Viagra® to opioids. The embodiments herein could be used in an acute medical ward or hospice, suitable for cancer patients.

The embodiments described herein change their delivery practices as the delivery device 104 goes through various stages of use. Wherever a user takes the delivery device 104 out of their mouth, some shrinkage may occur as some parking spots are partially collapsed, partly because of the vacancies created by the ingredients that have been released from their parking spaces. The result is that more ingredients may still be bio-available in the toothpick, but it may be necessary for a user to suck harder. This is because the more interior parking spaces require proportionally more pressure and saliva to be accessed. However, most humans have sufficient saliva to achieve this, and in fact may prefer to do so slowly, so that they can "meter" or "calibrate" the ingredient digestion process, somewhat similar to how a beer drinker may "nurse" a beer.

A typical consumer may be accustomed to a flavored toothpick lasting 5-6 minutes, being completed in one usage, and then tossed out. Accordingly, a change in consumer-mindset will be helpful in users developing a true appreciation for the delivery devices 104 described herein.

Specifically, users of the embodiments herein may find that they use the delivery device 104 in more than one usage-session. That is, they may put it in their mouth for e.g. 10 minutes, get is partly saliva-soaked, set it down (not throw it away), do something else, and then re-insert it for another 10 minute period. The whole consumer-mindset will change as consumers adapt to this 20-25 minute thresholds described herein, as opposed to the earlier, outmoded "disposal item" mindset.

Packaging, Shelf Life, Blooming, Paper, and Plastic

The embodiments herein may be individually wrapped in water resistant medical grade paper, or varied counts in polypropylene tubes or mylar bags. It may be possible to treat the paper, or treat the tube itself, so that the container(s) do not absorb the active ingredients of the flavorings. These active ingredients may sometimes include terpenes.

The interior of the tube-containers may be manufactured with Kemamide® E Ultra in bead form, "Erucamide" or "13-Docosenamide, (Z)-" so as to resist absorbing the flavoring or other ingredients (which may or may not be in the form of terpenes). It may be advantageous to use paper with an inlay that is resistant to leaching into the packaging. Citrus flavors contain ingredients which are known for jumping or dispersing from the original product. As such, citrus flavors pose some interesting packaging challenges.

In an embodiment, a medical-grade paper is used to individually wrap the delivery devices 104, including but not limited to medical grade paper such as what is used with sutures in or scalpel or a surgical needle. It is also possible to use a polypropylene wrap, a plastic rubber type of material that resists bacteria and enhance sterilization.

When people think about citrus, they think about air freshener, e.g. car freshener, because it "jumps". Citrus has auto-kinetic properties suitable for leaving its packaging to create a scent, an effervescence. Meanwhile, the embodiments disclosed herein need to keep it in, to prevent "jumping". Using the example of Mountain Dew®, it is a significant accomplishment that the product avoids separating into 13 layers. The same principle applies for inside packaging, make it taste fantastic but also last potentially as long as 2 years, depending on the specific flavorings and ingredients. The canna-products discussed herein might sit on a shelf for 2 months, but regular dry mouth formulations could sit on the shelf for 2 years.

A tube that holds multiple delivery devices 104, e.g. 21 devices, can be made from e.g. polypropylene (although the embodiments herein are not limited to polypropylene, and other compositions may also be used). Whether cast or molded, a problem called "blooming" can arise in a variety of ways. When plastic enters a certain state, i.e. when the plastic solidifies, it creates a soft layer on the inside of a mold. Thus, regardless of whether using extrusion molding, injection molding, or 3D printing, blooming may still be possible, because blooming is mainly temperature-based.

A similar comparison is on the inside of a cap of a container of Gatorade®. It's got a waxy coat. That active ingredient "blooms" to the top, so when sealing a bottle of Gatorade® lemon lime flavor, the citrus doesn't escape or "jump". The embodiments herein aspire to the same effect inside of their packaging, e.g. tubes. These embodiments are aimed at people that slide items into the inside of their jeans pocket, or inside their coat.

The embodiments herein are carefully calibrated to ensure long shelf life by using polypropylene bags which don't have that problem because the paper on the clear coat already has that waxy coating.

Using coating on the paper that the inside layer of the tube has the effect of that the citrus won't "jump". Citrus is difficult. To get the distinct flavor of lemon or orange, the terpenes of citrus are heavy. They separate. Oil and water separate. A goal is to deliver the best flavor experience. The average company using food grade flavorings, where 15% of a terpene reaches a user's mouth. In sharp contrast, the embodiments herein are near 77-80% effective delivery to a user's mouth, which means the terpenes will be highly concentrated. Any true flavoring terpene, whether in a candle or whether it's in an air freshener, is going to separate.

In an embodiment, it is possible to add different emulsifiers and weighting agents to keep the citrus bonded to the delivery device 104. The weighting agents don't prevent the separation, but they slow it down, and can help a solution stay distributed, for up to e.g. 45 minutes.

Specifics of THC

The THC embodiments described herein carry some special challenges. In an embodiment, THC is originally purchased in a semi-solid state, but where separation may occur. Further, state by state requirements regarding THC purity vary widely. A THC supplier may perform a high-volume extraction and then split up the various components. However, a purchased THC product may also occur the other way around, where several THC extractions were performed, and then combined. The end result is that the extractions may be inconsistent, may separate or diffuse, and may be impure.

Next, in some U.S. states, suppliers are not required to indicate information regarding purity, while in other states, requirements exist. Further, these laws and requirements are expected to change over time. That is, both THC extractors and also THC testing laboratories are still going through growing pains, inconsistent test results, reliability problems, and lack of a true understanding of the basic chemistry necessary to ensure consistent and uniform results. Even in 2018 and 2019, some in the THC service industry still have the philosophy and mind-set of taking pride in having been "underground" for many years. As such, they may look with disdain on ordinary testing processes and take an odd pride in avoiding scientific rigor, operating more by instinct than by professionalism.

Such THC businesses are being "weeded out" over time, but until the canna-industry achieves a better level of standardization, the embodiments herein will incorporate extra levels of testing and purity standards, and verification of chemical properties of all components at numerous places in the manufacturing process.

A first indication of problems when purchasing THC batches is that one can quickly detect quality issues merely by looking at the difference in colors (separation) in a single bottle in which different batches may have been combined. Further variation can be introduced if a testing service is not consistent in their practices. Next, test results can be difficult to coordinate across multiple batches.

Next, setting aside THC for a moment, some infusion blends need to be shaken more than others. For example, the lemon-lime embodiment needs to be shaken a lot more. To address this, it is possible to use a centrifuge.

Separation of the fluids used in the infusion process described herein is a constant concern, whether with the various THC embodiments or otherwise. If separation occurs over a 45 minute infusion-window, the resulting products would vary in concentration and quality. Ingredients added that enhance and make consistent viscosity and solubility are important. Consistency has everything to do with stabilizing ingredients prior to the actual infusion-window. The ingredients must also stay stable on the shelf, while awaiting participation in the processes discussed herein.

Moving back to the THC marketplace, the purchasers of the products herein have an expectation of a specific strength and delivery platform. Much like their rivals in the tobacco industry, the customers and end-users of the THC embodiments described herein have very set expectations about their end-products, and tend to give a very lively and unpleasant reaction when these expectations are not met.

Regarding use of toothpicks as the delivery device 104, it is necessary to make assumptions of a certain number of milligrams of dosage per toothpick. That is, if a manufacturer is targeting 30 mg of ingredient, that manufacturer has to be sure they are going to achieve the desired 30 mg. This industry is carefully regulated, especially with regard to THC.

Three Rounds of Testing

The embodiments herein incorporation numerous testing procedures. The following example will use a THC/CBD model, but the testing principles described therein could be applied to many other ingredient platforms and formulations. Accordingly, at least three rounds of testing should be the SOP on any active ingredients as they help justify any changes possible in the constants. The steps in between and the items being added create the variables, thus allowing us to adjust in the process A) Summary 1) First steps—(Verification of THC/CBD cannabinoid potency),—on average 2 mg of THC/CBD oil is selected to test from new batch acquisition. Once received into the states inventory system ingredient is sent for lab analysis. Within 48-72 hours the lab will provide a full analysis of the cannabinoid test results. Do not go forward with further infusion or other work until the test results come back after 48 hours. If the test results are bad enough, scrap that bottle, label it non-compliant, perhaps ask for a refund, but do not use that specific bottle.

From these test results, it is possible to determine the formulations and exact dosage targets desired for each batch.

2) Second steps—(small batch infused picks testing) 40 mL test tubes are used with approximately 25 picks to test new formulations. After infusion process and drying is completed, 5 random samples are sent for lab analysis, or the lab analysis is performed on-premises.

3) Third—(product batch runs and testing) Full recipe solutions are prepared to match desired results from testing. Production solution is then used for full batch infusions. After infusion process and drying is completed, 5 random samples are sent for Lab analysis drop off or pick up. Results are stored for retailer and state inquiries.

These results of these three tests have to mirror each other. If not, the reasons for inconsistencies have to be addressed and removed.

B) Details of Testing

A jar of THC may cost $900, which if properly infused should result in e.g. $8,000 of product. However, if the jar-metrics are off by 20%, that could cost a manufacturer e.g. $1600. Further, the loss and damage is not limited merely to a number of toothpicks. There is also reputational damage, as a customer just had that much less of it experience because they're not getting their expected 30 mg of THC. That is, that customer might get 30 mg of something, but it may not be the THC concentration they are expecting. They might get 30 mg of a 70% concentration, which will have a different effect than the 30 mg of 90% concentration they were expecting. These expectations also hold true for their expectations regarding flavorings, and even size or thickness of the delivery device 104.

Upon receipt of a new bottle of THC-solution (usually sold in a liquid form), it is necessary to send out a sample from that bottle immediately, to determine how much milliliters of fluid transfer into milligrams of THC that can be transferred onto a delivery device 104. Due to potential separation, it may be necessary to shake the new bottle and\or it into a centrifuge prior to taking the sample. This yields information as to how to modify the various percentages for a manufacturer to produce compliant batches of liquid solution to be applied in an infusion process. That is, modify the infusion solution, be it using more\less ethanol, more\less solvent, more\less water, or something else, and then also send out that modified sample, for another round of testing. When reusing a fluid, a second batch may have 10-20% drop-off, and third and fourth batches may decrease potency even more, but they can still be used.

This completes the description of the first phase of THC-testing.

After small batching (small amounts of xfers to toothpicks), a second phase of testing will be performed on the delivery device 104 and within 48 hours will have results how much milliliters (of fluid) transferred into milligrams (within a particular toothpick). As part of increasing accuracy of a manufacturing process, will take that variations found in the second phase, modify the percentage of e.g. THC used in a formulation for the larger batch. Find the difference, and test again.

This completes the description of the second phase of THC-testing.

A third phase of THC-testing will be on (ostensibly) completed delivery devices 104. The third test will be applied to delivery devices 104 post-infusion, and should closely resemble products that will reach the marketplace.

So it's not just "test", then "test", then "test again". Instead, "test", "modify solution if necessary", "test again", but also "modify processes if necessary", and then "test again", before product goes out the door for sale to consumers.

The processes described herein at times leave a small buffer, and for customer-satisfaction tend to err on the side of the giving slightly more ingredient to the customer, rather than less. As such, a 30 mg toothpick in a (purported) 30 mg batch, might actually contain 31 or 32 mg of ingredient.

In an embodiment, a Gas Chromatography Mass Spectroscopy (GCMS) device may be used to test for THC. It may be advantageous to have this GCMS equipment located at the infusion-site, so that the turn-around can be achieved more quickly. For example, the 48-72 hour testing-delay alluded to earlier could be reduced to e.g. 6 hrs.

Distributed Manufacturing ("Scaling" the Company)

Next, the manufacturing steps and processes described herein are mean to be transportable, scalable, and distributable. It is possible to have an employee or third-party service do manufacturing runs at a first location according to instructions from a main coordinating area in a different location. The remote staff may know some aspects of the process, but do not need to know all aspects. Using this type of procedure, there are less complication, less education and skills necessary on the part of the worker, but also less risk of loss, theft, or misappropriation of proprietary manufacturing information. That is, the person running this process will know a couple of their steps, e.g. time of infusion. But they will not know much else. They will not need to know, or figure out, how compound AA may become soluble with compound YY.

In one embodiment, the testing equipment e.g. Gas Chromatography Mass Spectroscopy (GCMS) is off-site. This may increase delays in production, but makes the manufacturing equipment more portable and movable. In another embodiment, the testing equipment is on-site. This may result in more accurate, faster production runs.

A manufacturing instruction may be e.g. "apply pre-treat powder", where no more detail is given. Items may be labeled merely as "flavor", "base", "active ingredient A", "active Ingredient B", or something else generic yet descriptive. Also include testing results from labs, showing full-profile testing. Not so much for the specific data therein but to show veracity, diligence, and level of sophistication.

Caffeine

In working with caffeine, it is necessary to heat up the water high enough to get caffeine to go into solution therewith. Thus, for caffeine embodiments, heated water acts as a solvent. Then, the oven temperature set so that it doesn't boil out the caffeine.

Caffeine is not very soluble at room temperature, so those products might be mixed at e.g. 190 degrees.

Solvents

Regarding these ingredients, it is sometimes necessary to infuse the delivery device-product with multiple combinations of ingredients, some of which resist such combination. To overcome this, a solvent may be used to combine the ingredients One such solvent is ethanol, chemical symbol $C_2H_6O$. Ethanol has the advantage of a low molecular weight, which means it is more volatile. Solvents, such as but not limited to ethanol, ensure that the ingredients arrive properly, and get properly parked in the parking spaces.

There may be a small amount of baking soda still present when the solvent arrives, but this is expected to be minor. As stated, some baking soda may be intentionally left in the delivery device for the purpose of altering the pH of the ingredients within the delivery device 104.

Another resource used within the embodiments herein is a combination of ethanol (as a solvent) and sucrose acetate isobutyrate (SAIB, a weighting agent which uniformly distributes a non-polar solute in a polar solvent).

Ethanol is used as a solvent but it shouldn't have any interaction with the baking soda. They are put in at different times. The parking spaces are first created with the baking soda, the baking soda is then removed (using e.g. dry heat in a baking oven). Only after that point are the active ingredients introduced.

Jambu oleoresin and CBD are soluble in ethanol. Meanwhile, xylitol is soluble in water, but not in ethanol. As such, a great variety of solvents are needed for the variety of embodiments disclosed herein, due to the wide variety of ingredients subject to the infusion processes described herein.

User-Controllable Micro-Dosing

A non-treated toothpick might weigh approximately 0.24 grams (or 240 mg). The pre-treated picks described herein may have a mass of about 0.34 grams (340 mg), which is a 40% increase in mass. This includes all of the ingredients, whether xylitol, sucralose, caffeine, THC, etc. The ratio of ingredients to wood is around 10/24. However the dosage capacity would be less than this, because the total mass also includes additional ingredients besides the primary ingredient (e.g., THC, CBD, caffeine, nicotine, etc.). The dosage (ingredients) to wood ratio would also differ based on the type of wood used, the structure of the lignin within that wood, and size of molecules. Specifically, the dosage-wood ratio would decrease for ingredients having larger molecules.

The concentration of Jambu in the solution in which the toothpicks are soaked is 10,000 ppm or 1%. However, this doesn't tell the whole story. A toothpick absorbs about 0.12 mL of solution during processing. This would equate to 0.0012 mL (0.01×0.12 mL) of Jambu in a single toothpick. The mass of an average treated toothpick is 0.25 grams or 250 mg. The ppm (by mass) of Jambu in a toothpick is about 3500.

For comparison, beverages can have 30 to 60 ppm (0.003%) Jambu. Using the lower concentration, 30 ppm, multiplying 0.00003×355 mL, the volume of a 12 oz beverage, a person would consume 0.011 mL of Jambu—7 times the amount they would get from one toothpick, 14 times if using the upper value of 60 ppm. Chewing gum, on the other hand, can have 3,000 ppm. A stick of gum has a mass of 47,100 mg; at 3,000 ppm this equates to approximately 140 mg (or 0.14 mL) of Jambu—over 90 times the dosage of one toothpick!

The point of all this more controllable dosing is achieved by the embodiments herein. If a user wants some caffeine, but not an over-load, the embodiment herein are much more suitable for micro-dosing.

A consideration for a direct comparison of a toothpick with gum and beverages, as well as other food items, is that food items are typically swallowed, so the entire dosage of Jambu is ingested. These amounts are considerably higher than what is present in a single toothpick. Additionally, the Jambu in a toothpick is released slowly (over a period of at least 30 minutes) and mixed with saliva, which further reduces the concentration significantly. To consume the equivalent dosage of Jambu in a 12-oz beverage, a person would have to eat (chew up and swallow) around 10 toothpicks, in the same amount of time a person could drink a soda. Compared to a stick of gum, it would be 90 toothpicks.

Figure 8:
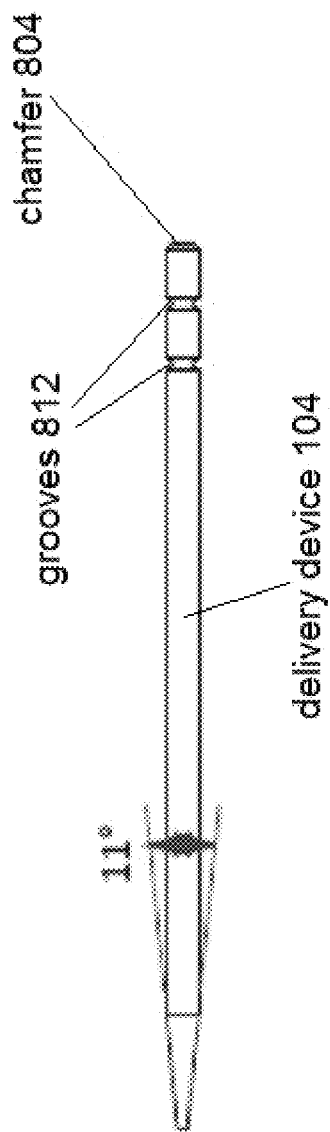
FIG. 8 shows an example delivery device in the shape of a toothpick, specifically, a semi-pointed double-grooved configuration.
Figure 9A:
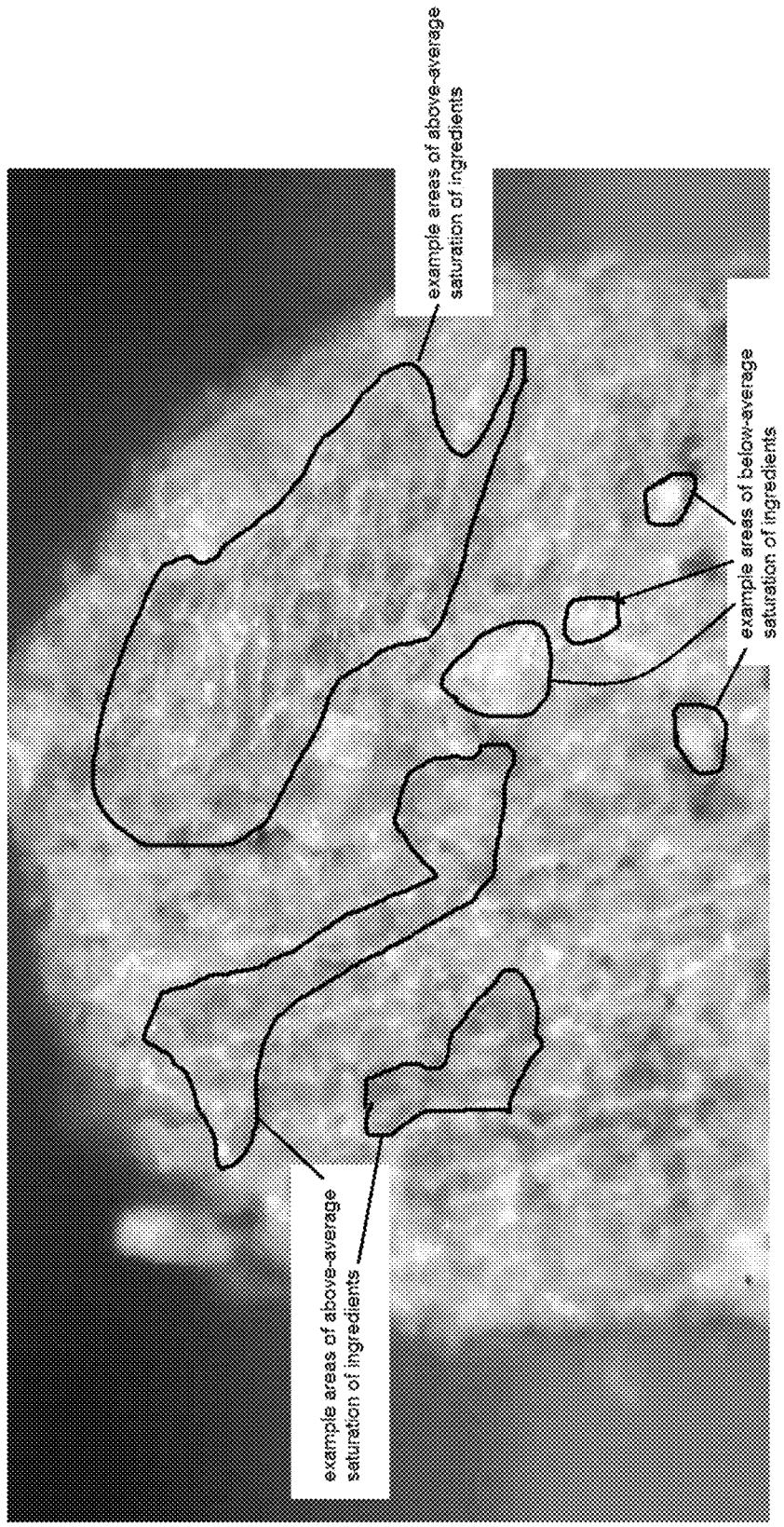
FIGS. 9A, 9B, 9C, 9D, and 9E show cross-sections a delivery device using varying types of dyes and specific ingredients.
Figure 9B:
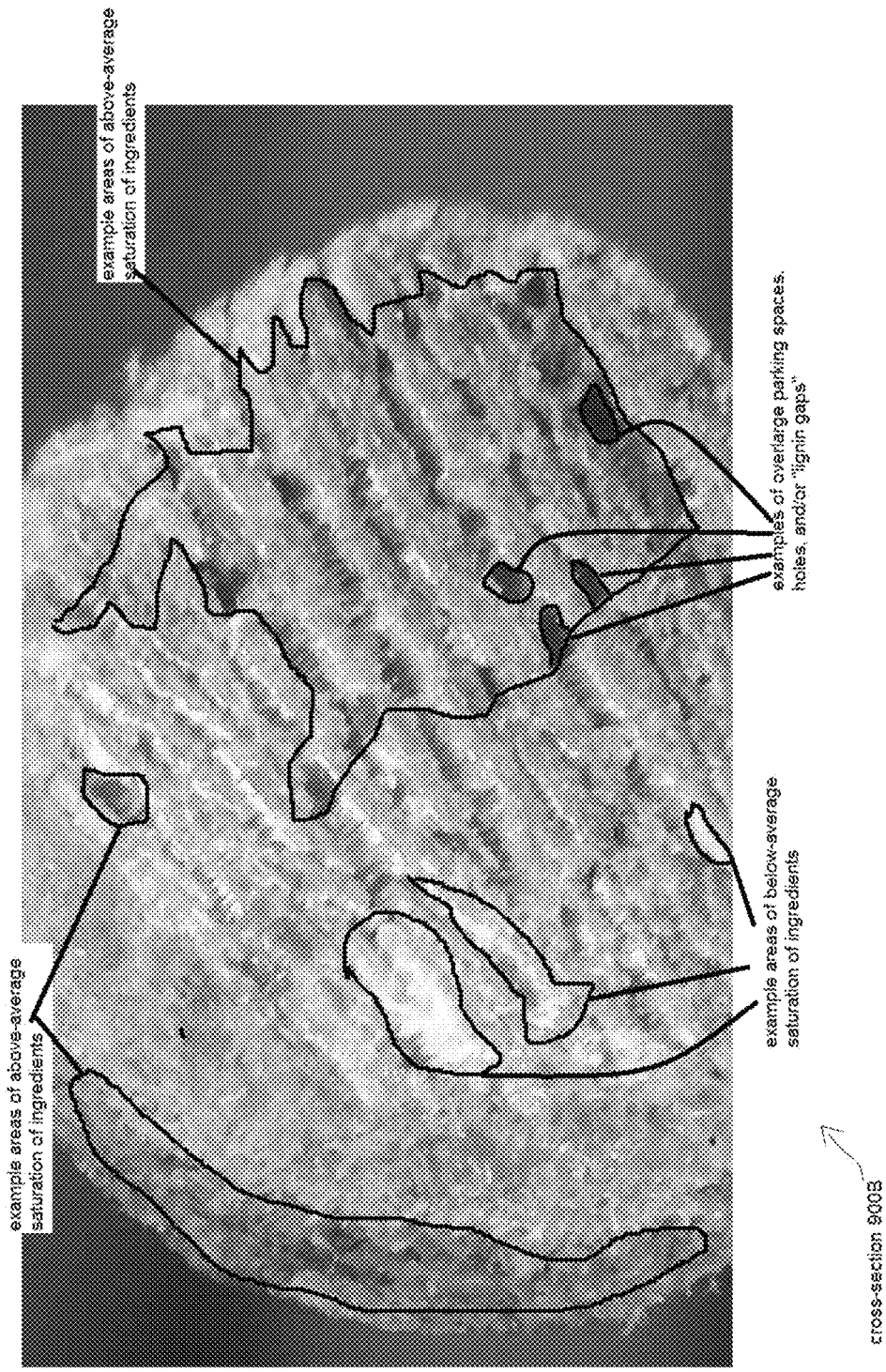
Figure 9C:
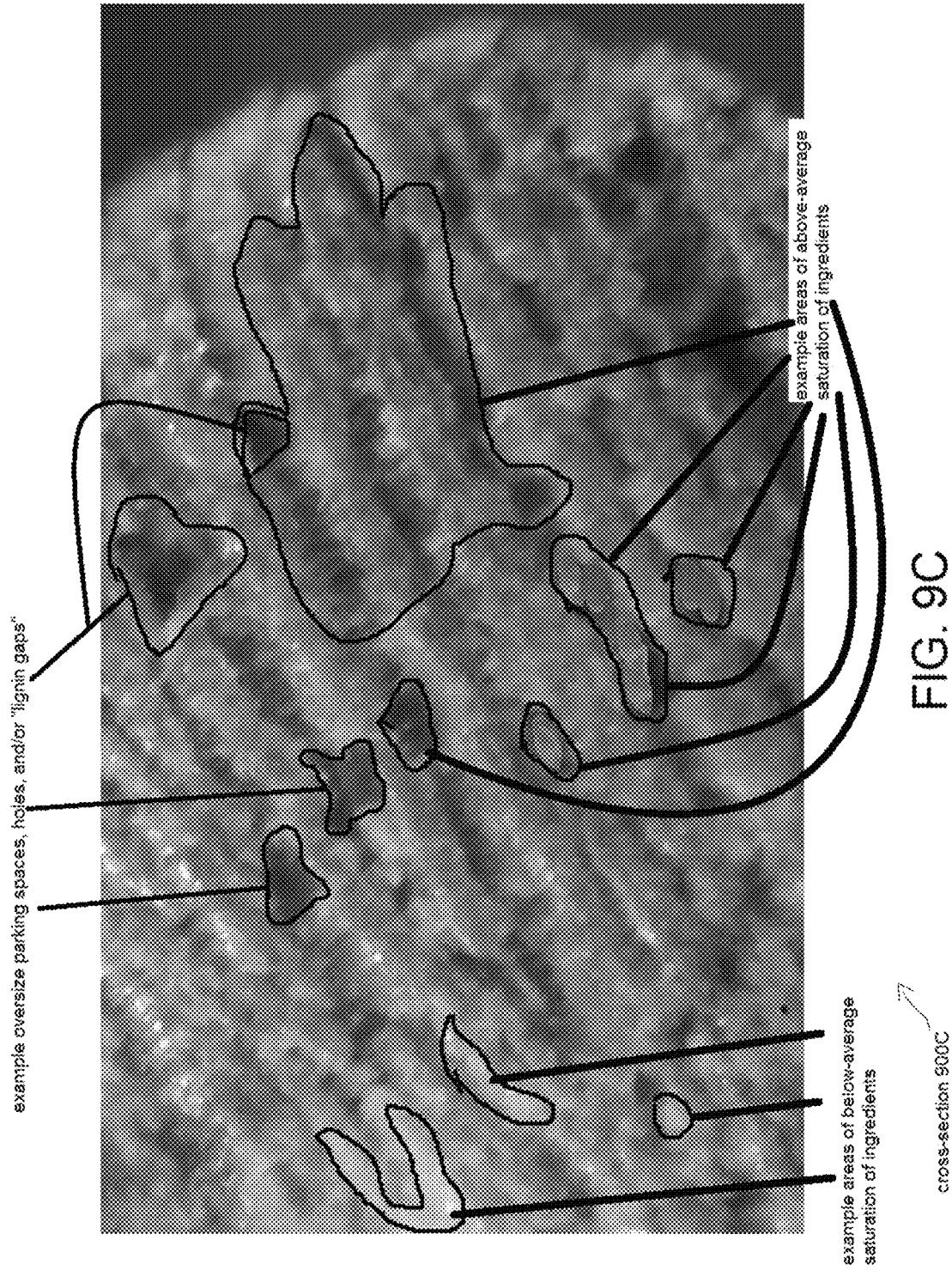
Figure 9D:
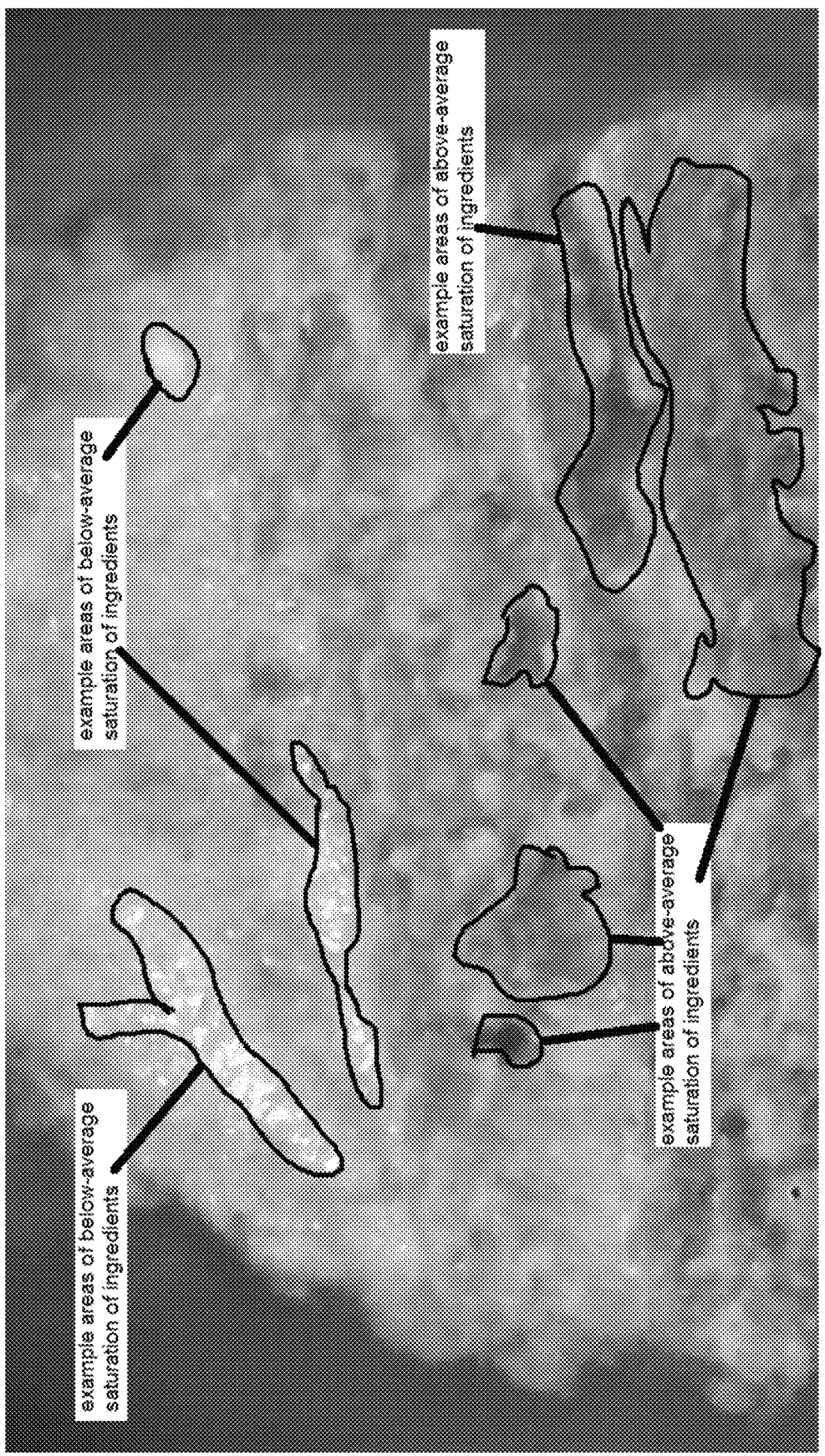
Figure 9E:
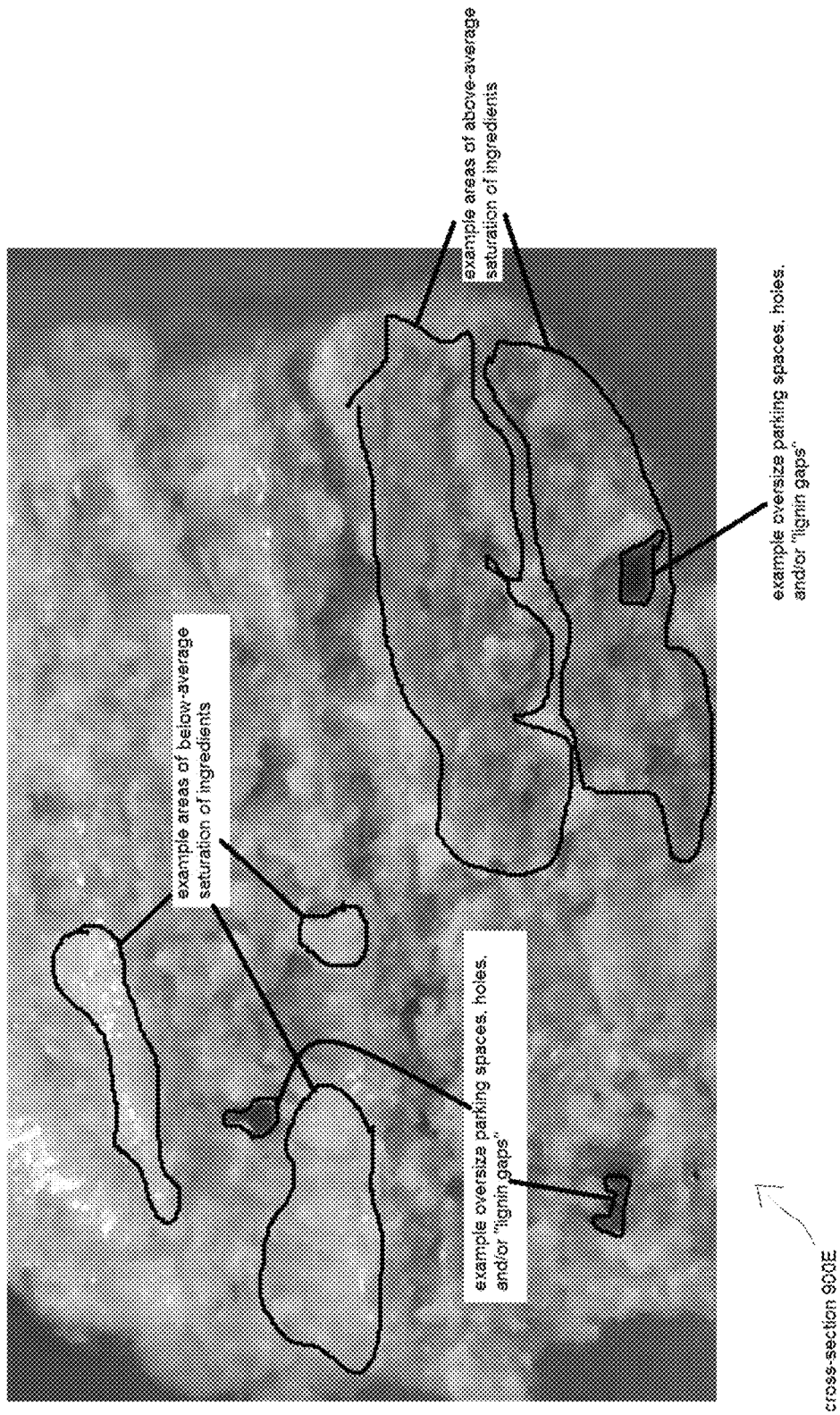

FIG. 8 shows an example delivery device 104 in the shape of a toothpick (specifically, a "semi-pointed double-grooved" configuration). The grooves are the two grooves at the rear (finger-hold) side, and the semi-pointed (not a full point) is at the front (insertion) side. It is important to note that many different toothpick designs could be used for the delivery device 104, so that the embodiment shown in FIG. 8 is but for example only.

However, the FIG. 8 embodiment does have some advantages. For example, the specific width has been found to be better for shipping, and the two grooves 812 can in some cases make the delivery device 104 more amenable to being handled by machine-vision processing devices. Further, customer-tests reported the 11 degree angle gave a slightly better "mouthfeel". The 11 degree angle provides improved stability and uniformity in cutting and machining. The manufacturing process machines can count the picks as they come out, in some cases using these two grooves 812 as markers or spacers. The, the grooves 812 are not just random grooves, but provide a specific advantage. Similarly, the chamfer 804 aids in packaging and handling of the delivery devices 104 during transport.

Further embodiments include a more flared back-end surface with, for example, knurled flare-pads. This would be in the case of users with limited manual dexterity, fingers missing, or for persons with palsy or other problems with gripping, etc. As such, residents of nursing homes, assistive living places, people with war injuries, diabetes, or other persons having limited use of finger-tips could still use the delivery device 104 to self-administer their medications.

Along these same lines, it is also possible to have a toothpick-shape with a slight-Y at the rear (finger) end, so the user could spin it in their mouth a bit, and handle it better.

Penetration Charts

Another type of product testing is contemplated in which a delivery device 104 is cut laterally. FIGS. 9A-9E show cross-sections 900A-E of a typical delivery device 104, using varying types of dyes and specific ingredients. The dyes help in providing visible evidence that the specific ingredients penetrate effectively to the center and interior regions of the delivery device 104.

Ideally, the penetration of the testing-dyes corresponds with penetration of the active ingredients. However, it is noted that with the wide variety and composition of ingredients discussed herein, a wide variety of testing-dyes should be employed, to ensure good compatibility and lack of separation.

These dye-penetration read-outs can then be compared with similar market products, such as other CBD, THC, dry mouth, and/or smoking cessation toothpicks. As shown in FIG. 3, the primary locus of active ingredients within conventional toothpicks reaches only to the outer rings and does not achieve the penetration to the inner rings shown in FIGS. 9A-9E. Along with this goes the fact that the conventional products reach the saturation exhaustion limit much quicker than the delivery devices 104 described herein. Also that these devices do not have "parking spots", and do not show signs of altered lignin.

Regarding the dyes, these must stay consonant with and achieve the same penetration as the active ingredients such as CBD, THC, drymouth, and/or smoking cessation stay in solution and achieve the same exact penetration as the active ingredients. The dyes must not get either ahead of or behind the penetration of the active ingredients, and also must have some kind of visible characteristics that can show in the wood, and be clearly attributable only to the dye itself and not to some other factor. Thus, the reliability of such cross-sectional images is only as good as the dye-accuracy and effectiveness.

Example dyes that could be used to perform this include polar and/or non-polar dyes. The type of photography used might be visible-spectrum, infra-red, or ultraviolet. In an embodiment, cross-sectional cut-testing can be regularly performed to ensure quality of ingredient-load within a specific production run of delivery devices 104. In the event a production run is found to be faltering or improper, the specific techniques used in that production run can be reviewed in order to trace back and correct any variations or anomalies with the production process, or determine that the ingredients are faulty or mis-applied.

The embodiments herein strive for consistency. However, when dealing with wood and its lignin, some minor variations are to be expected, and yet remain within acceptable boundaries. One example of variations are could be overlarge parking spaces, holes, or "lignin gaps" in the interior of a delivery device 104. Such variations are part of the reason why five separate FIGS. 9A-9E are shown to illustrate the principle of effective penetration.

All wood items have a minimal amount of random composition, including occasional holes and gaps, but the embodiments herein control this randomness to be within tolerable limits, so as to ensure a measurably consistent amount of ingredients packaged within any particular delivery device 104. The embodiments herein are very careful to control for both overloads and underloads, testing and process-management at numerous stops along the way through the manufacturing process.

Also, regarding overlarge parking spaces, holes, or lignin gaps, it is noted that these cross-sections showing these holes or gaps are deliberately taken at random intervals within the length of any given delivery device 104. As such, it should not be assumed that such holes or gaps extend the entirely length of the delivery device 104.

What is claimed is:

1. A method of infusing a delivery device, comprising:
pre-treating the delivery device with baking soda, and forcing water and baking soda into an interior of the delivery device, thereby making alterations to a lignum structure and an interior structure of the delivery device;
locating a plurality of ingredients within the delivery device;
testing the delivery device for the predetermined presence thresholds and predetermined concentration thresholds of the plurality of ingredients;
packaging the delivery device;
pretreating the delivery device to increase the porosity of the delivery device, thereby creating parking spaces;
hardening the delivery device; and
after hardening, removing the baking soda by rinsing, but leaving the parking spaces.

2. The method of claim 1, further comprising:
preparing an infusion solution containing the plurality of ingredients; and
infusing the substrate with the infusion solution in a pressure- and temperature-controlled environment at predetermined pressures, temperatures, and durations.

3. The method of claim 1, further comprising:
arranging that the treatment solution remains evenly mixed, homogenous, and does not settle or break down.

4. The method of claim 1, further comprising:
arranging that the treatment solutions penetrates through the entire delivery device, and is evenly distributed throughout the entire delivery device and not merely surface-only or near-surface-only absorption.

5. The method of claim 4, wherein the infusion solution further comprises binding agents.

6. The method of claim 4, wherein the infusion solution further comprises sweeteners.

7. The method of claim 4, wherein the infusion solution further comprises weighting agents.

8. The method of claim 1, further comprising:
after the step of testing, depending on the results of the testing, re-infusing the delivery device.

9. The method of claim 4, further comprising:
incorporating a testing dye into the infusion-solution;
cutting a cross-section of a plurality of delivery devices;
photographing the plurality of delivery devices along their cross-sectional cut; and
examining the cross-sectional cuts to determine level of penetration of the ingredients.

10. The method of claim 9, further comprising:
after the step of examining, depending on the results of the examining, re-infusing the delivery device.

11. The method of claim 1, comprising:
one of the ingredients in the infusion solution comprising Jambu oleoresin.

* * * * *